United States Patent [19]

Okumura et al.

[11] 3,974,211
[45] Aug. 10, 1976

[54] METHOD OF MANUFACTURING METHALLYL SULFONATE

[75] Inventors: Osamu Okumura, Funabashi; Katsumi Yaguchi, Tokyo; Ikuo Adachi, Chiba; Masuzo Nagayama, Tokyo, all of Japan

[73] Assignee: Lion Fat & Oil Co., Ltd., Tokyo, Japan

[22] Filed: Jan. 8, 1975

[21] Appl. No.: 539,413

Related U.S. Application Data

[63] Continuation of Ser. No. 385,054, Aug. 2, 1973, abandoned.

[30] Foreign Application Priority Data

Aug. 7, 1972 Japan.............................. 47-078996

[52] U.S. Cl............................................. 260/513 T
[51] Int. Cl.$^2$..................................... C07C 143/16
[58] Field of Search ................................ 260/513 T

[56] References Cited
UNITED STATES PATENTS

| | | | |
|---|---|---|---|
| 2,335,193 | 11/1943 | Nawiasky et al. | 260/513 T |
| 2,365,783 | 12/1944 | Suter | 260/513 T |
| 3,205,237 | 9/1965 | Blaser et al. | 260/513 T |
| 3,694,493 | 9/1972 | Lorenz et al. | 260/513 T |

OTHER PUBLICATIONS

Gilbert, "Sulfonation and Related Reactions", pp. 16–18 (1965).

Primary Examiner—James O. Thomas, Jr.
Assistant Examiner—Nicky Chan
Attorney, Agent, or Firm—Woodhams, Blanchard and Flynn

[57] ABSTRACT

A method of manufacturing methallyl sulfonate, which comprises: forming a sulfur trioxide-dialkyl sulfoxide complex by effecting reaction between sulfur trioxide and dialkyl sulfoxide as mixed at the ratio of more than 0.8 mol of the latter to 1 mol of the former in the presence of an inert solvent; effecting reaction between said complex and isobutylene, in an amount of 0.9–1.2 mols of isobutylene per 1 mol of sulfur trioxide, by applying a temperature in the range of 10°–80°C; and neutralizing the reaction product with a base.

7 Claims, No Drawings

METHOD OF MANUFACTURING METHALLYL SULFONATE

This is a continuation of application Ser. No. 385,054, filed Aug. 2, 1973, now abandoned.

BACKGROUND OF THE INVENTION

The present invention relates to a method of manufacturing methallyl sulfonate, and particularly it relates to a method of manufacturing methallyl sulfonate wherein a dialkyl sulfoxide-sulfur trioxide complex is employed for sulfonation of isobutylene.

Methallyl sulfonate is an important monomer to be combined with acrylonitrile to form a copolymer, and as to the method of manufacturing thereof, there have hitherto been proposed a variety of methods. One of them is a method wherein isobutylene is first chlorinated and then the resulting methallyl chloride is made to react with sodium sulfite. This method, however, is accompanied with a relatively large quantity of sodium chloride as the by-product having a harmful effect on the polymerization of methallyl sulfonate. Another method intended for direct sulfonation of isobutylene wherein reaction between isobutylene and sulfur trioxide is to be effected in a liquid sulfur dioxide at −20°C has been disclosed on page 787 of Bull. Soc. Chim. France (1965). This method, however, is of no practical use inasmuch as it produces a large quantity of isobutylene polymer as the by-product. As the method of sulfonating isobutylene by the use of a certain $SO_3$ complex, there are known such a method as disclosed on page 978 of J. Am. Chem. Soc. 63 (1941) wherein sulfur trioxide-dioxane complex is to be employed and a method as disclosed in Japanese Pat. Publication No. 41527/1971 wherein sulfur trioxide - alkyl amide complex is to be employed. However, according to the former method, not only is it difficult to maintain the complex stable, but also the accompanying by-products in large quantities remarkably lower the yield of the intended product. As to the latter method, on the other hand, though it is possible to stably maintain the complex employed and effect its reaction with isobutylene, it is defective in that it is indispensable to use excess alkyl amide in effecting said reaction and the methallyl sulfonate produced thereby gets somewhat colored, so that it is not always suitable.

The present invention is intended for improvement of the method of sulfonating isobutylene employing sulfur trioxide - dialkyl sulfoxide complex, and is to provide a method rendering it possible to obtain an uncolored methallyl sulfonate in high yield by virtue of the employment of sulfur trioxide - dialkyl sulfoxide complex. Application of sulfur trioxide - dialkyl sulfoxide complex as the sulfonating agent has so far been tried on special alcohols, and in such cases, the presence of excess dialkyl sulfoxide is indispensable in order to stably maintain the complex. Besides, even when the complex is thus maintained stably, it is impossible to obtain the sulfonate in high yield. But, the inventors of the present invention have found the fact that, said sulfur trioxide - dialkyl sulfoxide complex is suitable for use in sulfonation of isobutylene which is different from ordinary sulfonation reaction in that methallyl sulfonic acid is to be produced through sultone, and employment of this complex for sulfonation of isobutylene followed by neutralization renders it possible to manufacture an uncolored methallyl sulfonate in high yield.

SUMMARY OF THE INVENTION

The present invention is to provide a method of manufacturing methallyl sulfonate, which comprises: forming a sulfur trioxide - dialkyl sulfoxide complex by effecting reaction between sulfur trioxide and dialkyl sulfoxide to be expressed by the general formula

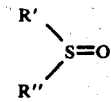

(wherein R' and R'' represent alkyl radical having 1–8 carbon atoms) as mixed at the ratio of more than 0.8 mol of the latter to 1 mol of the former in the presence of an inert solvent; effecting reaction between isobutylene and said complex as mixed at the ratio of 0.9 – 1.20 mols of the former to 1 mol of sulfur trioxide composing the latter by applying a temperature in the range of 10°–80°C; and neutralizing the reaction product with a base.

In the present invention, the ratio of sulfur trioxide composing the complex to dialkyl sulfoxide to react with each other is at least 1:0.80 in terms of molar ratio. When the quantity of dialkyl sulfoxide is less than this value, appropriate mitigation of the reactivity of sulfur trioxide is infeasible, resulting in failure to prevent the object product from getting colored. The reaction between sulfur trioxide composing the complex and dialkyl sulfoxide is effected in the presence of an inert solvent. The inert solvent herein means a solvent capable of stably maintaining the formed complex and substantially free from reacting with isobutylene. In this connection, hydrocarbons, halogenated hydrocarbons, liquid $SO_2$, dialkyl sulfoxide and the like are suitable for use as the inert solvent in the present invention. The quantity of these inert solvents to be employed for the present invention is required to be at least sufficient for dispersing the complex therein, and this quantity may be determined by judging from common sense of those skilled in the art.

According to the present invention, the sulfur trioxide - dialkyl sulfoxide complex and isobutylene dispersed in an inert solvent are supposed to react with each other as set forth above, and the quantity of isobutylene to be added is in the range of 0.9 – 1.20 mols per 1 mol of sulfur trioxide. In the case where the quantity of isobutylene is less than the minimum of the foregoing range, there will remain some unreacted sulfur trioxide, while in the case where said quantity is more than the maximum of the foregoing range, there will remain some unreacted isobutylene, and therefore both cases are undesirable. The temperature for sulfonation reaction in the present invention is to be adjusted within the range of 10° – 80°C. In the case where the reaction temperature is lower than 10°C, the reaction speed will be low and the yield of the intended product will decrease, while in the case where the reaction temperature exceeds 80°C, not only a part of the methallyl sulfonic acid produced will be decomposed, but also the final product will be remarkably colored, and therefore both cases are undesirable.

The sulfonated product is subsequently neutralized with a base and becomes methallyl sulfonate as the final product. As the base for this purpose, either of the organic base and inorganic base is applicable, but, generally speaking, application of the alkali metal hydroxides or organic amines is preferable.

As explained in the foregoing, according to the present invention, methallyl sulfonate can be manufactured by employing a sulfur trioxide - dialkyl sulfoxide complex under such reaction conditions as may be set easily. Particularly, according to the present invention, a complex best suited for sulfonation of isobutylene can be obtained without employing superfluous mols of dialkyl sulfoxide relative to sulfur trioxide, and, inasmuch as this dialkyl sulfoxide is comparatively stable against a base as the neutralizer, it is possible to obtain an uncolored methallyl sulfonate. In this connection, according to the above referenced method disclosed in Japanese Pat. Publication No. 41527/1971 wherein the use of a sulfur trioxide - alkyl amide (as represented by dimethyl formamide) complex is taught, it is required to employ superfluous mols of alkyl amide relative to sulfur trioxide, and, the instability of this alkyl amide as compared with dialkyl sulfoxide seems to be a cause of the coloring of methallyl sulfonate, the object product. Consequently, taking this fact into consideration, the present invention is an excellent method of manufacturing methallyl sulfonate.

Hereunder will be given further particulars of the characteristic feature of the present invention with reference to examples embodying the present invention.

DESCRIPTION OF THE PREFERRED EMBODIMENTS

EXAMPLE 1

The present example is illustrative of the influence of the reaction temperature upon the sulfonation reaction.

29 g of dimethyl sulfoxide (DMSO) was first dissolved in 150 g of dichloroethane, and then 30 g of sulfur trioxide was added to the resulting solution over the period of about 30 minutes at the temperature of 10°C. The molar ratio of DMSO to $SO_3$ on this occasion was 1.00. Next, the solution was heated up to 30°C and subjected to vigorous agitation for about 1 hour. To the thus prepared dichloroethane suspension of DMSO-$SO_3$ complex, 22 g of liquefied isobutylene having the temperature of 25°C was added. The molar ratio of isobutylene to $SO_3$ on this occasion was 1.15. Subsequently, the resulting mixture was subjected to vigorous agitation for 1.5 hour for aging, followed by removal of dichloroethane through evaporation at 40°C under reduced pressure and neutralization with 43 g of an agueous solution of 35 wt.% caustic soda to the extent of the pH value of 7.5. Further, upon removal of DMSO and water through evaporation, the neutralized residue was dried, whereby a white product was obtained. When this product was subjected to extraction with 90% ethanol, sodium salt of methallyl sulfonic acid could be extracted in a fixed quantity.

The temperature for sulfonation reaction, the yield ratio of sodium salt of methallyl sulfonic acid relative to $SO_3$ and the whiteness of the product were as shown in Table-1 below. In this context, the measurement of the whiteness was conducted in accordance with the APHA evaluation process for 10% aqueous solution.

Table 1

| Test No. | 1 | 2 | 3 | 4 | 5 |
|---|---|---|---|---|---|
| reaction temperature (°C) | −10 | 10 | 50 | 70 | 90 |
| yield ratio (%) | 52 | 73 | 97 | 95 | 83 |
| whiteness | less than 5 | less than 5 | less than 5 | 10 | 50 |

As will be clear from the foregoing table, in the case of Test-1, there is observed a lowering of the yield, and in the case of Test-5, there is observed deterioration of the whiteness.

EXAMPLE 2

The present example is illustrative of the influence of the quantity of dialkyl sulfoxide employed upon the sulfonation reaction.

Dimethyl sulfoxide (DMSO) was first dissolved in 200 g of dichloroethane, and then 40 g of $SO_3$ was added to the resulting solution over the period of about 40 minutes at the temperature of 20°C. Next, the solution was subjected to vigorous agitation for about 1 hour, whereby DMSO—$SO_3$ complex was formed to perfection. Thereafter, to the thus formed complex, 29.3 g of liquefied isobutylene having the temperature of 20°C was added. The resulting mixture was then subjected to vigorous agitation for 1 hour for aging, followed by removal of dichloroethane through evaporation at 40°C under reduced pressure and neutralization with 57.3 g of an aqueous solution of 35 wt.% caustic soda to the extent of the pH value of 7.5. Further, upon removal of DMSO and water through evaporation, the neutralized residue was dried, whereby a white product was obtained. When this product was subjected to extraction with 90% ethanol, sodium salt of methallyl sulfonic acid could be extracted in a fixed quantity.

The quantity of DMSO employed, the yield ratio of sodium methallyl sulfonate relative to $SO_3$ and the whiteness of the product were as shown in Table-2 below. In this context, the measurement of the whiteness was conducted in the same way as in Example 1.

Table 2

| Test No. | 6 | 7 | 8 | 9 |
|---|---|---|---|---|
| quantity of DMSO (g) | 23.4 | 31.2 | 39 | 78 |
| (molar ratio of DMSO to $SO_3$) | (0.6) | (0.8) | (1.0) | (2.0) |
| yield ratio (%) | 81 | 94 | 96 | 96 |
| whiteness | 40 | 8 | less than 5 | less than 5 |

EXAMPLE 3

The present example is illustrative of the influence of the molar ratio of isobutylene to $SO_3$ upon the sulfonation reaction.

Upon forming DMSO—$SO_3$ complex by adding 40 g of $SO_3$ to 150 g of DMSO over 40 minutes' period at the temperature 40°C, the complex was vigorously agitated for 1 hour. Subsequently, to the thus agitated complex, liquefied isobutylene having the temperature of 40°C was added, and the mixture was subjected to aging at 50°C for about 1 hour, followed by neutralization with 57.3 g of an aqueous solution of 35 wt.% caustic soda to the extent of the pH value of 7.5. Thereafter, by removing DMSO and water through evaporation and drying the neutralized residue, there was obtained a white product. When this product was subjected to extraction with 90% ethanol, sodium salt of methallyl sulfonic acid could be extracted in a fixed quantity.

The quantity of isobutylene employed, the yield ratio of sodium methallyl sulfonate relative to $SO_3$ and the whiteness of the product were as shown in Table-3 below. In this context, the measurement of the whiteness was conducted in the same way as in Example 1.

Table 3

| Test No. | 10 | 11 | 12 | 13 | 14 |
|---|---|---|---|---|---|
| quantity of isobutylene (g) | 22.4 | 28 | 30.8 | 33.6 | 39.2 |
| (molar ratio of isobutylene to $SO_3$) | (0.8) | (1.0) | (1.1) | (1.2) | (1.4) |
| yield ratio (%) | 78 | 97 | 98 | 97 | 85 |
| whiteness | 50 | less than 5 | less than 5 | less than 5 | less than 5 |

EXAMPLE 4

Upon forming DMSO—$SO_3$ complex by adding 40 g of $SO_3$ to 150 g of DMSO over 40 minutes' period at the temperature of 30°C, the complex was vigorously agitated for 1 hour. Subsequently, to the thus agitated complex, 31 g of liquefied isobutylene having the temperature of 25°C was added, and the mixture was subjected to 1 hour's aging at 50°C, followed by neutralization with 100 g of an aqueous solution of 40 wt. % caustic soda at the temperature of about 50°C. The resulting neutralized mixture was then left standing to get separated into two layers. 170 g of a mixed liquid comprising DMSO and water was recovered from the upper layer. The lower layer was cooled down to 10°C, whereby 63 g of sodium methallyl sulfonate was isolated as precipitate. The filtrate obtained on this occasion contained about 17 g of sodium methallyl sulfonate, 20 g of caustic soda and 42 g of water, and it was reused as the neutralizer in the second test conducted through the same procedure as set forth above. In the second test, there was obtained the precipitate of sodium methallyl sulfonate at the yield ratio of 93% relative to $SO_3$ applied. This precipitate had the purity of 99% in terms of soidum methallyl sulfonate, and contained 1% of inorganic salt (Glauber's salt).

EXAMPLE 5

By dissolving 74 g of butyl propyl sulfoxide in 150 g of dichloroethane, adding 40 g of $SO_3$ to the resulting solution over 30 minutes' period at the temperature of 35°C and then vigorously agitating for about 1 hour at the same temperature, a complex was formed. Subsequently, after adding 29.5 g of liquefied isobutylene to said complex, the resulting mixture was subjected to 1 hour's aging at the temperature of 50°C, followed by neutralization with 57.3 g of an agueous solution of 35 wt.% caustic soda to the extent of the pH value of 7.5. After removing dichloroethane, water and butyl propyl sulfoxide therefrom, the neutralized mixture was washed with ethanol, whereby a white product was obtained. The dry weight of this product was 74 g, and the yield ratio thereof relative to $SO_3$ applied was 92%.

COMPARATIVE EXAMPLE

Test was conducted under the same conditions as in Test-12 of Example 3 except for application of 140 g of dimethyl formamide in lieu of 150 g of DMSO used in Test-12, whereby a light-yellow product was obtained. The yield ratio of sodium methallyl sulfonate relative to the theoretical yield of $SO_3$ employed was 94%, and the whiteness of the product as measured through the same evaluation process as in Example 1 was 30.

As a result of copolymerization effected by the conventional method upon adding 1.9% of methallyl sulfonate to a mixture of monomers comprising acylonitrile and methyl acrylate at the molar ratio of 93:7, there was obtained but a light-yellow polymer in the case where methallyl sulfonate obtained in the present example was employed while there was obtained a white polymer in the case where methallyl sulfonic acid obtained in Test-12 was employed.

What is claimed is:

1. A method for preparing methallyl sulphonic acid, which comprises reacting sulfur trioxide with dimethyl sulfoxide, at a molar ratio of more than 0.8 mol of said dimethyl sulfoxide per 1 mol of sulfur trioxide, in the presence of a liquid solvent which is inert to isobutylene, to form a stable suspension of sulfur trioxidedimethyl sulfoxide complex in said solvent; and then reacting, in said solvent, at a temperature in the range of 10° to 80°C, said complex with isobutylene, at a molar ratio of 0.9 to 1.2 mols of isobutylene per 1 mol of sulfur trioxide in said complex, to produce a reaction product containing methallyl sulphonic acid.

2. A method as claimed in claim 1 in which said solvent is liquid $SO_2$.

3. A method as claimed in claim 1 in which said solvent is a hydrocarbon.

4. A method as claimed in claim 1 in which said solvent is a halogenated hydrocarbon.

5. A method as claimed in claim 1 in which said solvent is dimethyl sulfoxide.

6. A method according to claim 1 in which the molar ratio of dimethyl sulfoxide to sulfur trioxide is from 0.8 to 2.0 and the solvent is dichloroethane.

7. A method as defined in claim 1, wherein said inert solvent consists of dichloroethane and the molar ratio of sulfur trioxide to dimethyl sulfoxide is about 1:1.

* * * * *